United States Patent [19]

Donnelly et al.

[11] 4,377,436
[45] Mar. 22, 1983

[54] PLASMA-ASSISTED ETCH PROCESS WITH ENDPOINT DETECTION

[75] Inventors: Vincent M. Donnelly, Berkeley Heights; Daniel L. Flamm, Chatham Township, Morris County, both of N.J.

[73] Assignee: Bell Telephone Laboratories, Incorporated, Murray Hill, N.J.

[21] Appl. No.: 318,329

[22] Filed: Nov. 5, 1981

Related U.S. Application Data

[63] Continuation of Ser. No. 149,503, May 13, 1980, abandoned.

[51] Int. Cl.$^3$ .................. H01L 21/306; C23C 15/00
[52] U.S. Cl. ........................... 156/626; 156/643; 156/646; 156/657; 204/192 E
[58] Field of Search ............... 156/626, 643, 657, 627, 156/646; 204/192 E

[56] References Cited

U.S. PATENT DOCUMENTS

| | | | |
|---|---|---|---|
| 4,246,060 | 1/1981 | Keller | 156/643 |
| 4,312,732 | 1/1982 | Degenkolb et al. | 156/643 |
| 4,328,068 | 5/1982 | Curtis | 156/626 |

OTHER PUBLICATIONS

Curtis et al., "End Point . . . Spectroscopy", J. of Electrochemical Society, vol. 125, (5/78), pp. 829-830.
Alcorn, "Determining . . . Holes", IBM Technical Disclosure Bulletin, vol. 19, No. 3, (8/76), pp. 982-983.
Harshbarger et al., "A Study . . . Etching", Applied Spectroscopy, vol. 31, No. 3, (1977), pp. 201-207.
Stafford et al., "Optical . . . Stripping", Solid State Technology, (9/77), pp. 51-55.
Desilets, "Multiple . . . Detector", IBM Technical Disclosure Bulletin, vol. 21, No. 3, (8/78), pp. 1035-1037.
Hoekstra, "Metal Etch Monitor", IBM Technical Disclosure Bulletin, vol. 14, No. 9, (2/72), pp. 2680-2682.
Khorury et al., "Front . . . System", IBM Technical Disclosure Bulletin, vol. 20, No. 5, (10/77), pp. 1756-1759.
Horiike et al., "A Dry . . . Microwave", Electrochemical Society–Semiconductor Silicon, (5/77), p. 1071ff.

Primary Examiner—Jerome W. Massie
Attorney, Agent, or Firm—Eugen E. Pacher

[57] ABSTRACT

Endpoint detection during plasma-assisted etching is signalled by cessation or onset of spatially confined luminescence resulting from an etch reaction product. Sensitivity of the system is aided by an optically focused detector which selectively detects such fluorescence as associated with one or a small number of lithographic features.

24 Claims, 1 Drawing Figure

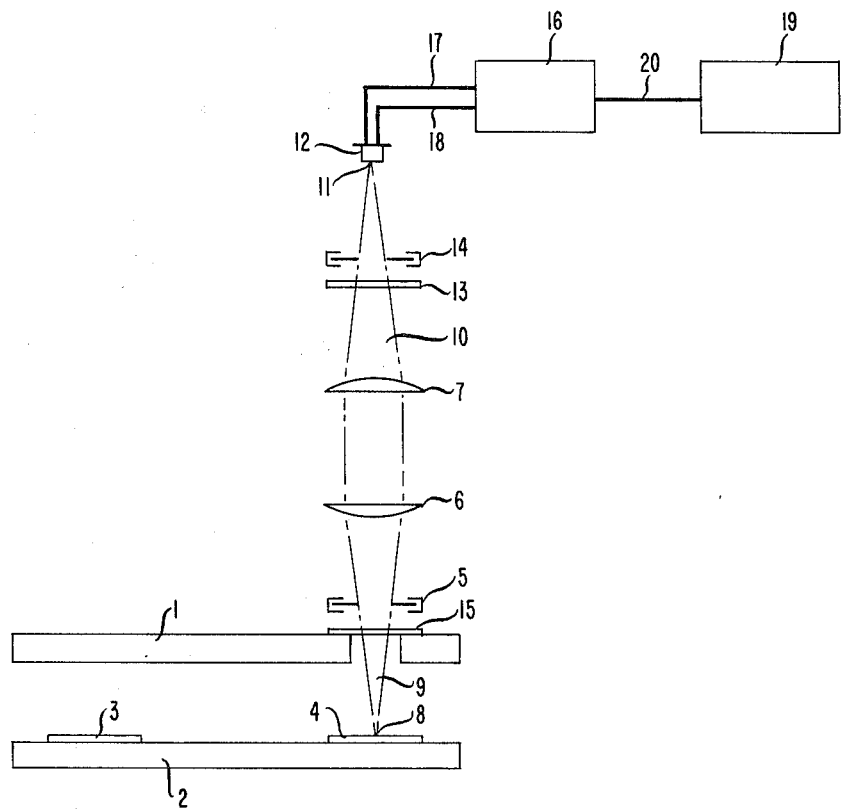

PLASMA-ASSISTED ETCH PROCESS WITH ENDPOINT DETECTION

This is a continuation of application Ser. No. 149,503 filed May 13, 1980, now abandoned.

BACKGROUND OF THE INVENTION

A. Technical Field

The field of the invention is best described as entailing lithographic delineation by selective removal of portions of continuous layers. Of particular concern is the fabrication of integrated circuits, particularly silicon integrated circuits. Fabrication of such circuits involves selective removal of elemental silicon, silicon-containing compounds, as well as associated materials, such as, aluminum conductor.

B. History

Large Scale Integrated circuitry and particularly that involving silicon (Silicon Integrated Circuits) represents a high level of sophistication. Commercial circuitry is based on design features of three or four micrometers. Circuit chips a fraction of an inch in size may contain fifty thousand or more elements. Experimentally designed and constructed circuits are based on still smaller feature size. The emerging level known by some as Very Large Scale Integrated circuitry contemplates chips with hundreds of thousands of elements or even a million elements.

Many types of processing are involved in the construction of LSI devices. SIC's, for example, entail a wide array of deposition and other material addition procedures. Regardless of the type of circuitry, all manufacture involves etching—first in delineation of masking layers and, finally, in delineation of device material layers. Selectivity, whether by removal or addition, is generally based on extremely precise delineation brought about by etch-removal of selected regions of continuous layers. These etch procedures (including those specific to resist removal—sometimes called resist development) have necessarily kept pace with device miniaturization and must be considered the critical determinant of both presently available and prospective levels of integration.

Wet etching in which selected removal results from differential solubility or selected baring of material to be removed relies on a variety of agents—both organic and inorganic. Wet etching continues to be a significant factor. At the resist pattern delineation level, wet etching, more commonly called wet development, is prevalent.

To an increasing extent, wet etching is yielding to dry etching. Advantages, of increasing significance for further device miniaturization include reduction in amount of residue. Inherent lithographic advantages include a high degree of resolution, as well as some degree of control over etch profile.

Many recent developments involve systems specific to the variety of materials to be removed. A significant category of systems are based on etchant species which directly or indirectly involve charged particles or other unstable particles produced through electrical discharge across a vapor medium. Such plasma assisted processes take a variety of forms depending on electrical input (power, frequency, etc.) and depending on apparatus design (electrode size, spacing). Plasma-assisted etching is often carried out within or adjacent to the luminescent region of the plasma. See, C. M. Melliar-Smith and C. J. Mogab in *Thin Film Processes* J. L. Vossen and W. Kern, eds. Chap. V-2 Academic Press, New York (1978). A variant involves "downstream etching" in which plasma produced species contact material to be removed only at a position downstream of the active discharge.

LSI devices undergoing fabrication involve delineation of layers which may be a micrometer or less in thickness. Spacings between regions to be removed may be a very small number of micrometers. Development of plasma chemistry with a high degree of discrimination as between material to be removed and retained, as well as systems which permit anisotropic or other desired profiles have been required and are generally acceptable. More and more, feasibility of finer design rules, commensurate with reasonable yield, have depended upon other considerations.

Discrimination and profile control often require monitoring. For example, etching should be stopped when underlying material has been bared. Failure to reach this "endpoint" may destroy device function; while exceeding it may result in lateral attack on etch walls to result in undercutting or "bottoming". Monitoring, and particularly endpoint detection is a significant part of the technology.

Endpoint detection may take the form of detection of an impedance change. Impedance, as measured across the discharge region, is altered by presence in kind and amount of etchant species as well as by fragments produced by wanted or unwanted material removal. An alternative endpoint detection approach is based upon emission within the plasma. Such measurement may be based on emission from an excited plasma species—e.g., on emission from a plasma etched species which changes amplitude based on the degree of consumption during etching. An example is monitoring based on the 703.7 nm emission line of impact-excited atomic fluorine. Both procedures are used to advantage—both are limited: (a) both involve small differences in relatively large quantities; (b) both entail averaging and consequently may not indicate certain types of product failure.

SUMMARY OF THE INVENTION

The inventive advance depends upon local detection of luminescence associated either with wanted or unwanted product. Common to every aspect of the invention is a detector which is so focused on a region adjacent a surface undergoing etching, usually a relatively small circuit area (e.g., an area associated with one or a very small number of features considered particularly critical in terms of acceptable product). The invention depends upon luminescence associated with reaction product, with processing conditions chosen to result in luminescence close to the surface and in the immediate vicinity of etching. A preferred embodiment relies upon luminescence of reaction product excited during formation or by a subsequent event (reaction or impact excitation). This embodiment does not require any excitation means other than that involved in the plasma-assisted process.

Detection is carried out with the least apparatus complication in downstream etching. Such processing is removed from the discharge region and facilitates observation of specific emission. Processing in the plasma reaction chamber is also contemplated. Such procedures which permit the highest degree of profile control may require filtration—perhaps by interference or colored filters; perhaps by use of prisms or diffraction gratings.

An important embodiment is based on chemiluminescence resulting from reaction product generated in the presence of atomic fluorine. The associated intense well-defined luminescence is particularly useful in the fabrication of SIC's since most etch procedures entail removal of elemental silicon-bearing material, itself, or, in the alternative, removal of layered material overlying such material.

The various permitted modes—e.g., detection of etching endpoint, detection of etching onset, downstream detection, detection within the reaction chamber, etc., share a common characteristic. Since detection is based upon species evolved in the vicinity of the surface undergoing etching, loss of sensitivity due to dilution is lessened. Detection is localized to a particular surface region as well. focusing on a chip, on a subcircuit, or on a feature permits monitoring sensitive to local processing perturbations.

BRIEF DESCRIPTION OF THE DRAWING

The FIGURE is a schematic representation of apparatus suitable for the invention.

DETAILED DESCRIPTION

1. General

The inventive procedures have widespread applicability in the local monitoring of etch processes which inherently produce apropriate luminescent species. Alternatively, such species may be induced.

The inventive procedures share a characteristic as compared with other types of monitoring now in use. Since they all depend upon luminescence of reaction product (direct or indirect) which is confined to a small volume, intensity is high. Preferred embodiments rely upon conditions designed to optimize this confinement.

Aspects of the invention invariably rely on such confinement. This confinement, while dependent upon a number of processing parameters, is conveniently controlled commensurate with processing objectives primarily by use of sufficient pressures to prevent unwanted migration of emitting species from the immediate vicinity of the surface. In general, pressures so dictated are at a minimum a fraction of a Torr—of the order of $10^{-2}$ Torr or usually 0.1 Torr or higher. Such a minimum for many of the contemplated reactions/systems gives rise to a confinement of the order of a few millimeters or less (in terms of a drop off of emission to a level which is 1/e of maximum (e is the natural logarithm base $\simeq 2.7$).

An important aspect of the invention is concerned with confinement in a dimension parallel to the surface undergoing etching. The same processing parameters which prevent undue migration vertically lessen lateral migration. Proper specification of such parameters may result in a drop off in intensity to 1/e within a few millimeters or even within several micrometers of a feature being etched. The first range permits monitoring on a circuit or chip basis. Apparatus/systems subject to loading and attendant unequal etching may, therefore, be monitored selectively at the very chip position within the wafer which is most critical.

Designation of conditions to further lessen migration permits detection of subcircuits or even of individual features. Inhomogeneity in etch rates may be due to microloading and proximity effects and may become particularly significant where feature sizes are small (design rules permit dimensions 3.5 $\mu$m or smaller). Production yield may be dependent upon precise process control of a particular feature/s or subcircuit. Embodiments of the present invention permit monitoring on a scale appropriate to this dependence.

Detector design requirements are eased by species confinement with resulting high intensity. Detection of features of from 2-3 $\mu$m is permitted by microscope optics which may yield 5:1 contrast on this scale (4/5 of the gathered radiation from the designated feature area with only 1/5 from surrounding regions). Detection on a 10 $\mu$m scale offers no problem. Design criteria are available—see, for example, *Fundamentals of Optics*, by Jenkins and White, McGraw-Hill (1950).

Radiative events usefully employed may result upon initial reaction of etchant and surface. Examples deal with species excited subsequent to initial formation. In a preferred embodiment, the subsequent event is reaction to a higher oxidation state. Other subsequent excitation events involve impact with an electron or a larger particle. In all instances, reaction times, as well as excitation lifetimes, are sufficiently short that confinement is attained by restricting movement of concerned species under conditions appropriate for plasma etching.

The invention is generally defined and claimed in terms of local monitoring. By "local" is meant a volume significantly less than the entirety within the container (plasma chamber or downstream reactor). The local volume is in the vicinity of the surface being etched. The vertical dimension of the volume and also the lateral dimension (parallel to the surface) are both of the order of millimeters or less. In preferred embodiments, the lateral dimension may approach feature sizes of the order of a very few micrometers. The restricted volume which gives rise to improved sensitivity implies two constraints: (1) constraint on migration of material to avoid diffuse emission and (2) constraint on apparatus design to permit selective access to such restricted volume. The first is considered in terms of a fall-off in emission intensity to 1/eth of peak value; while the apparatus constraint is in terms of contrast of better than 50 percent and, preferably, of at least 75 percent (in usual terms, contrast is the ratio of radiation gathered from the designated area divided by the total light gathered).

It is expected that the invention will find use primarily in terms of endpoint detection. Endpoint may be signalled by a drop off or cessation in steady state luminescence due to emission from a species resulting from wanted etching. In the alternative, (or in combination), endpoint may be signalled by the onset of radiation from a reaction product due to unwanted etching (by reaction between etchant and material underlying material to be etched). Monitoring may also be usefully employed to signal the onset of wanted etching and even to monitor etch rates. Response to detected signal may be manual or automated. Design of feedback circuitry responsive to the usual electrical output signal of common detectors is conventional.

2. The FIGURE

The schematic illustration is representative of etching either in a reaction chamber or downstream of a reaction chamber. Members 1 and 2, in the former instance, may represent parallel plates with member 1 serving as the driven electrode and member 2 serving as the grounded electrode. Application of power to such plates, by means not shown, results in generation of a plasma between such members with confinement by an external vessel, also not shown. The plasma is struck across a suitable vapor composition, for example, the $CF_4/O_2$ mixture in prevalent use for elemental silicon etching. Wafers 3 and 4, if on the grounded electrode, may be undergoing processing by that plasma-assisted procedure known as plasma etching. (Members 1 and 2 of approximately equal area—plasma pressure a fraction of a torr $\geq 0.05$.) Detection is via an iris 5 and lenses 6 and 7 which, together, sense a restricted area schematically represented as focal point 8. Radiation collected initially as diverging beam 9 is converged as shown in beam portion 10 to result in a focal point 11 on detector 12. Optional filter 13 and iris 14 increase the signal-to-noise ratio, blocking transmission of wavelengths not associated with the determinative species and by restricting the solid angle to avoid scattered light, respectively. Optional element 15 may represent a closure and/or ancillary filter means. Electrical output from detector 12 is transmitted to amplifier or impedance-matching device 16 by leads 17 and 18 and from there to display and/or recorder means 19 as depicted by arrow 20.

3. Process Parameters

Contemplated processes are those in which monitoring follows radiative emission of a species resulting from reaction. Relevant procedures are generically classed as plasma-assisted etching. A variety of procedures of this type have evolved and have been assigned process designations. These include designations, such as "plasma etching", "reactive ion etching", "sputter etching", "ion milling", etc.

Procedures of the invention depend upon confinement of radiative species to regions of dimensions of the order of millimeters or less. This requirement imposes some restriction on permitted dispersion of radiating species. This, in turn, in many instances, imposes a pressure limitation which may preclude ion milling and certain other high vacuum procedures. In general, pressure requirements, which may range from $10^{-2}$ Torr to 20.0 Torr or more, limit relevant etch processes to those in which material removal is largely due to chemical reaction rather than momentum transfer. Examples were conducted under conditions usually associated with "plasma etching". Processing parameters are generally dictated by the etching process, itself. Commercial significance certainly involves silicon device fabrication, and typical etch systems are those suitable to such fabrication. An example involves monitoring via the chemiluminescent specie resulting from reaction between elemental silicon and a plasma-derived fluorine species. Suitable plasma compositions include those resulting from introduction of $CF_4/O_2$, $C_2F_6O_2$, $CF_3Cl/O_2$, $NF_3$, $ClF_3$, $SF_6/O_2$, and $SiF_4/O_2$.

Discussion of processing parameters suitable for use with these chemical systems, as well as a variety of others, are available from the literature. See, for example, 49 Applied Phys. 3796 (1978); 22(4) Solid State Tech. 109 (1979); 126 J. Electrochem. Soc. 464 (1979); 17 Japan J. Appl. Phys. 235 (1978).

4. Apparatus

Again, apparatus is that suitable to the etch procedure, per se. Parallel plate reactors and barrel reactors are described in *Thin Film Processes* supra. Downstream etching is described in Semiconductor International page 60 (1979). Other apparatus designs suitable to the etch procedures may be substituted.

The primary apparatus modification introduced is provision for optical sensing. Regardless of the apparatus used, an optical path for radiation of the wavelength emitted by the relevant radiating species is needed. In the usual apparatus, the path takes the general form depicted in the FIGURE and includes a window transparent at least to radiation to be detected.

5. Examples

Examples are discussed in terms of a parallel plate reactor of a design in commercial use (for general description, see A. R. Reinberg, "Etching for Pattern Delineation" (H. G. Hughes and M. J. Rand, Editors) *The Electrochemical Society, Inc.*, Princeton, N.J. (1976). the reactor includes a suitable vacuum enclosure and means for applying power, generally in the radio frequency range (e.g., ~13 MHz). Broad faces of the electrodes are horizontal; the lower plate is maintained at ground potential and serves as support for wafers undergoing processing. The plates are similar in area and power is applied to the upper plate so that it becomes "driven".

Pressures are generally maintained within the range of from 0.1 to 2.0 Torr. Flow rates are in the range of 10 to 500 sccm (standard cubic centimeters per minute). Power as applied to 17-inch diameter electrodes is in the range of 100 to 3,000 watts. Electrodes are spaced from 5 to 50 mm apart and substrate temperature is generally within the range of 25–250 degrees C.

Various processing parameters are adjusted to yield acceptable etch rates. Rates of 300 Angstroms/min. are generally sufficient for LSI manufacture. Upper limits are generally imposed by increasing nonuniformity.

The standard parallel plate reactor is modified to provide for optical access, as schematically depicted in the FIGURE. Consistent with general requirements for practice of the invention, the optical system has a point of focus within a few millimeters of the surface region to which it is directed. It consists of a pair of lenses and a bandpass filter in the 400–700 nm region designed to discriminate against atomic and molecular fluorine emission bands between 500–800 nm. The lens system is designed to image an area ~1 mm in a lateral dimension. Fluorescence to which the silicon photodiode detector and filter combination are sensitive includes a continuum peaking at 632 nm with a full width at half intensity of 240 nm. Such radiation represents the chemiluminescence resulting from etching elemental silicon in a fluorine-containing plasma.

EXAMPLE 1

A 3-inch silicon wafer coated, in turn, by a $SiO_2$ layer and a 0.3 $\mu$m layer of polysilicon masked by photoresist with bared regions of minimum dimension ~3 mm is etched within a plasma derived from introduction of $F_2$ under conditions:
~200 watts
1.0 torr
10 mm electrode spacing
25 degrees C. lower electrode temperature
50 sccm flow rate of
10 volume percent $F_2$ remainder He.

Under these conditions, etch rate is approximately 1000 Angstroms/min.

Upon attainment of steady state conditions, the particular detector arrangement develops a voltage of 10 mv at the silicon detector output. The voltage is seen to drop off to a level of 1 mv after a period of approximately 3 min with reduction from the steady state voltage to the lowered voltage occuring over a period of 15 sec. Etching is stopped, the wafer removed, and a feature within the field of view of the optical system is examined. The now bared SiO$_2$ layer is fully revealed and bottoming is negligible (etch walls have a profile which is substantially uninterrupted at the poly-SiO$_2$ interface.

EXAMPLE 2

A masked 3-inch silicon wafer coated by a 0.3 μm layer of SiO$_2$ is placed on the lower electrode and exposed to a plasma-derived atmosphere resulting from introduction of C$_2$F$_6$—10% O$_2$. Etching conditions are generally as outlined. The steady stage voltage developed by the detector is at a level of approximately 10 mv. After a period of approximately 3 min., the voltage developed at the output side of the detector rises to a level of 1 volt in a period of 30 sec. Cessation of etching, again, reveals features characterized by clear silicon area and continuous side wall profile.

EXAMPLE 3

A downstream etch process using the general reactor conditions as outlined in Example 1 is carried out with appropriate equipment modification providing for downstream passage of plasma produced species to a vessel within which etching is carried out. Conditions in the downstream vessel are 10 torr, 1000 sccm. As in Example 1, a steady state detector output voltage of 100 mv is attained very shortly after commencement (after a period of about 30 sec.). After 3 min., the steady state output voltage is found to drop off to a level of 1 mv over a period of 30 sec. Cessation of etching, removal of sample, and inspection are generally as described in Example 1.

We claim:

1. Process for fabrication of an article comprising at least one operation during which the article undergoing fabrication comprises a layer of first material to be etched in at least one preselected region, the layer of first material being overlying a second material to be retained, the first material being etched primarily by a chemical reaction with at least one reactive species produced by a plasma within a plasma reactor, the plasma resulting from imposition of an electrical field across a vapor medium between electrodes, the etching being monitored by means including detection of electromagnetic radiation emitted by an excited species formed as a consequence of a chemical interaction between a species and article material in the preselected region, the means comprising optical path means for illuminating a detector with such radiation, and detector output means, characterized in that (a) the optical path means sense substantially only radiation emitted from within a restricted first volume of space adjacent the preselected region, with a contrast of at least 50%, the volume having lateral dimensions less than about 10 mm, and (b) the processing conditions are chosen to result in confinement of the excited species formed as a consequence of the chemical interaction to a second volume of space close to the preselected region, with at least a part of the first volume being within the second volume.

2. Process of claim 1 in which the layer of first material is partially masked, with the bared regions comprising the preselected region.

3. Process of claim 1 in which the optical path means includes focusing means.

4. Process of claim 3 in which the focusing means has a point of focus about 1 mm of the first material surface.

5. Process of claim 4 in which the field of view at the first material surface has a maximum lateral dimension of less than about 1 mm.

6. Process of claim 5 in which the maximum lateral dimension is less than about 10 μm.

7. Process of claim 1 in which the optical path means includes filter means for preferentially transmitting the radiation.

8. Process of claim 1 in which said first material or said second material comprises elemental silicon.

9. Process of claim 8 in which the optical path means includes a bandpass filter for selectively transmitting radiation within a continuum peaking at a wavelength of approximately 632 nm.

10. Process of claim 8 in which the article undergoing fabrication is etched within the plasma reactor.

11. Process of claim 8 in which the article undergoing fabrication is etched downstream of the plasma reactor.

12. Process of claim 8 in which the first material comprises elemental silicon.

13. Process of claim 12 in which the detection means serves to signal etching endpoint due to reduction in amplitude of the radiation.

14. Process of claim 8 in which said second material comprises elemental silicon.

15. Process of claim 14 in which the detection means serves to signal etching endpoint due to increase in amplitude of said radiation.

16. Process of claim 1 in which the restricted volume substantially corresponds with the preselected region, the region including a small number of features including a feature of a minimum dimension which is the minimum dimension for all features to be etched.

17. Process of claim 16 in which the preselected region includes only a single feature.

18. Process of claim 1 in which the radiation is luminescence, with the emitting particle species being a product of the etching reaction which is excited during formation.

19. Process of claim 1 in which the radiation is luminescence, with the emitting particle species being excited by an event subsequent to formation of reaction product of the etching reaction.

20. Process of claim 1, in which the chosen processing conditions comprise a pressure within the plasma reactor between about 0.01 Torr and about 20 Torr.

21. Process of claim 20, in which the chosen processing conditions further comprise detection of the radiation from a transition having a relatively short lifetime such that the second volume of space extends at most several millimeters from the preselected region.

22. Process of claim 1, in which the restricted first volume substantially corresponds with the preselected region, the region comprising at least one feature which etches at a rate slower than the average etch rate of first material.

23. Process of claim 22 in which the lower etch rate is an artifact of the etch process as practiced within the apparatus.

24. Process of claim 22 in which the lower etch rate is at least partially due to small feature size.

* * * * *

UNITED STATES PATENT AND TRADEMARK OFFICE
CERTIFICATE OF CORRECTION

PATENT NO. : 4,377,436

DATED : March 22, 1983

INVENTOR(S) : Vincent M. Donnelly and Daniel L. Flamm

It is certified that error appears in the above—identified patent and that said Letters Patent is hereby corrected as shown below:

Column 3, line 30, "apropriate" should read --appropriate--. Column 8, line 4, "about" should read --within about--.

Signed and Sealed this

Seventeenth Day of May 1983

[SEAL]

Attest:

DONALD J. QUIGG

Attesting Officer

Acting Commissioner of Patents and Trademarks